United States Patent [19]
Orsing

[11] Patent Number: 5,476,630
[45] Date of Patent: Dec. 19, 1995

[54] METHOD FOR MANUFACTURING DENTAL ASPIRATORS

[76] Inventor: Ernst Orsing, Missionsgatan 12, 253 70 Helsingborg, Sweden

[21] Appl. No.: 137,172
[22] PCT Filed: May 6, 1992
[86] PCT No.: PCT/SE92/00292
   § 371 Date: Nov. 29, 1993
   § 102(e) Date: Nov. 29, 1993
[87] PCT Pub. No.: WO92/19437
   PCT Pub. Date: Nov. 12, 1992

[30] Foreign Application Priority Data

May 6, 1991 [SE] Sweden ................................ 9101387

[51] Int. Cl.⁶ .......................... A61C 17/06; B29C 47/00; B29C 53/30
[52] U.S. Cl. .......................... 264/508; 264/150; 264/151; 264/209.3; 264/566; 425/290; 425/296; 425/303; 425/326.1; 425/392; 425/396; 433/96; 604/902
[58] Field of Search .................... 425/290, 296, 425/302.1, 326.1, 303, 327, 532, 387.1, 388, 392, 539, 396; 264/508, 515, 150, 151, 167, 209.3, 286, 566, 568; 433/91, 96; 604/902; 285/4

[56] References Cited

U.S. PATENT DOCUMENTS

| | | | |
|---|---|---|---|
| 3,409,224 | 11/1968 | Harp et al. | 239/33 |
| 3,438,578 | 4/1969 | Peterson et al. | 239/33 |
| 3,751,541 | 8/1973 | Hegler | 264/90 |
| 3,780,944 | 12/1973 | Zubalik | 239/33 |
| 3,859,025 | 1/1975 | Maroschak | 425/326.1 |
| 4,184,831 | 1/1980 | Hegler et al. | 425/326.1 |
| 4,417,874 | 11/1983 | Andersson et al. | 433/508 |
| 4,509,911 | 4/1985 | Rosenbaum | 425/326.1 |
| 4,865,797 | 9/1989 | Jaruenkyla | 425/133.1 |

Primary Examiner—Jay H. Woo
Assistant Examiner—Joseph Leyson
Attorney, Agent, or Firm—Herbert W. Larson

[57] ABSTRACT

Method of manufacturing a dental aspirator by extruding a continuous tube with a bellows portion. The tube is angled to form a number of folds, each of which consists of two cup-shaped portions having concave surfaces facing each other. One cup-shaped portion is made smaller than the other, allowing them to be snapped together. The bellows are formed from the tube wall by chilled mold chains. At the same time, the tube is profiled to form an end portion at the suction end of the finished aspirator.

15 Claims, 8 Drawing Sheets

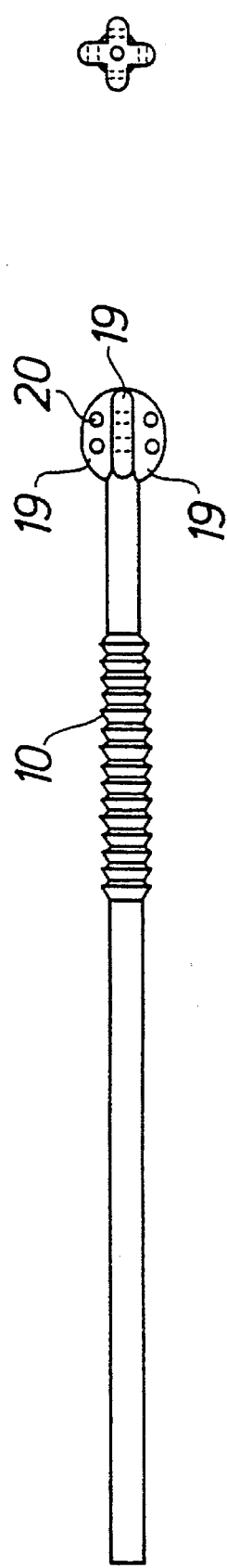

METHOD FOR MANUFACTURING DENTAL ASPIRATORS

BACKGROUND OF THE INVENTION

The invention relates to a method for manufacturing a dental aspirator comprising an extruded plastic tube which forms a bellows portion spaced from the ends of the tube and limited to a minor portion of the tube length, said portion allowing angling of the tube and comprising a number of folds each of which consists of two cupshaped portions which have the concave surfaces facing each other and one of which has a smaller width than the other one in order to be snapped completely or partly into said other cupshaped portion when the plastic tube is bent in the bellows portion, for maintaining the bow produced.

A dental aspirator of this type is described in U.S. Pat. No. 4,417,874. It is not disclosed therein how such a dental aspirator shall be manufactured but it may be assumed that the manufacture takes place in the manner which is conventional as far as suction tubes are concerned intended for the intake of liquid and provided with a bellows portion so that the end of the suction tube which is inserted into the mouth can be angled in relation to the end which is immersed into the liquid. These suction tubes have a diameter of about 8 mm and have a relatively thin wall, which is a prerequisite for the bellows portion being produced since this portion according to the common method of manufacture which is described in U.S. Pat. No. 3,409,224, is formed by the tube wall in a special work operation which is separated from the extrusion and must be performed in a separate machine, is pressed and deformed against an inner mandrel by means of rollers engaging the outside surface of the tube. This method of manufacture is suitable only for tubes having a thin wall, i.e. tubes having a wall thickness up to some tenths of a millimeter. However, when dental aspirators are concerned this wall thickness is too small because a tube having such a thin wall will be easily flattened during shipping and handling particularly when it is to be connected to a suction hose or if the dentist when working in the oral cavity incidentally presses against the dental aspirator. Moreover, such a tube does not have the necessary stability in the bellows portion so that the dental aspirator after having been bent to the desired angle and suspended on the lower cheek, tends to be straightened out if tension occurs in the connected hose or even only by the weight thereof. There is accordingly a pronounced need of a more stable but nevertheless easily bendable dental aspirator of the kind referred to above, which can be manufactured in a rational and profitable manner, because it is a matter of maintaining a low price of these dental aspirators which are a one way product and thus are scrapped after each use.

The purpose of the present invention is to satisfy said need. The method of the invention is based on the method applied for a very long time according to U.S. Pat. No. 3,538,209 in connection with large diameter tubes for inter alia sewers but also according to U.S. Pat. No. 3,751,541 for common suction tubes, in connection with the extrusion of a tube having a smooth wall to impart to said wall a corrugated shape by forming the tube wall against endless chilled mold chains under the influence of pressure or vacuum, said chains being moved in an endless path at each side of the still soft and warm tube leaving the extruder. In this method the corrugation thus is effected continuously over the total length of the tube (U.S. Pat. No. 3,538,209) or over limited portions of the tube (U.S. Pat. No. 3,751,541) in direct connection with the extrusion of the tube. However, in that case a simple corrugation is concerned including annular bulges with substantially semicircular cross sectional shape.

SUMMARY OF THE INVENTION

In order to achieve said object the method initially referred to has obtained according to the invention hereinafter described.

By this method which makes possible to manufacture a useable dental aspirator at low costs because the manufacture can take place continuously in one and the same machine without semi-finished products being transferred from one machine to the other as in case of rolling the bellows portion, there is achieved the additional advantage that the suction end of the aspirator which is located in the oral cavity and contacts the soft tissue can be shaped in such a way that the soft tissue will not be sucked into the dental aspirator, causing discomfort, and that this can be effected as a step in the continuous method of manufacture. It is common to provide the suction end of the dental aspirator with a separately manufactured (injection molded) cage-like plastic cover which is mounted on the otherwise completed aspirator by a separate work operation which sometimes is completely manual. An example of such a cover is disclosed in Re. U.S. Pat. No. 26470.

BRIEF DESCRIPTION OF THE DRAWINGS

In order to explain the invention in more detail reference is made to the accompanying drawings in which FIG. 4 is a side view of a second embodiment of the dental aspirator to be manufactured by the method of the invention, FIG. 5 is an end view of the embodiment in FIG. 4 from the suction end thereof, FIG. 9 is a fragmentary side view of the suction end of the dental aspirator according to FIG. 6 after a conical end portion has been snapped in.

DETAILED DESCRIPTION OF THE INVENTION

Figure 1:
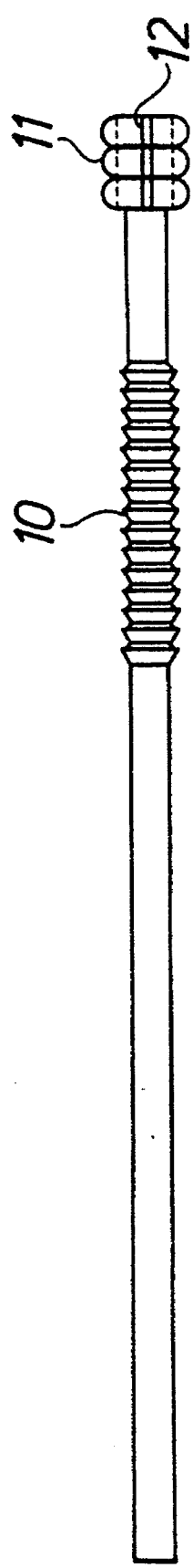
FIG. 1 is a sideview of a dental aspirator to be manufactured by the method of the invention.

FIG. 1 discloses a dental aspirator which can be manufactured by the method according to the invention. It can be made of PP or PE which are pro-environmental materials, but also PVC can be used for manufacturing the aspirator. The total length can be for example about 145 mm, and the aspirator is over the major portion of the length thereof made with smooth outside and inside surfaces but has an intermediate bellows portion 10 which can be for example about 45 mm in length and can be located at a shorter distance from the right hand end of the aspirator, which is the suction end thereof, than from the left hand end thereof, which is the end to be connected to a suction hose. The bellows portion 10 in a known manner shall include a number of folds each of which consists of two cupshaped portions, in this case two annular portions having the shape of truncated cones, which have the concave surfaces facing each other and one of which has a smaller width than the other one. The annular portions formed as truncated cones can be relatively articulated so that the bellows portion which in FIG. 1 is shown in an extended condition can be compressed by the portions of the smaller width are brought to snap below or into the portions with the greater width. Thus it is also made possible that the two portions located one at each side of the bellows portion, are angled in relation to each other, the annular portions shaped as truncated cones and having the smaller width at the inside of the bow are pressed partly under or into the annular portions shaped as truncated cones at the outside of the bow. A bellows portion of this type is extensively described in U.S. Pat. No. 4,417,874 referred to above.

The portions shaped as truncated cones and having the greater width have the small end thereof adjacent the end of the dental aspirator, which is to be connected to the suction hose, i.e. the left hand end in FIG. 1, which is the most advantageous embodiment because the folds inside the aspirator in the bellows portion then are directed the right way in relation to the flow direction through the aspirator and there is reduced tendency of whirl formation in the pockets present in this portion, such whirls reducing the suction power. The reversed arrangement of the portions shaped as truncated cones is however possible within the scope of the invention.

The dental aspirator has at the suction end thereof three or more gently curved annular bulges 11 which fulfill the same function as the cage-like cover of conventional dental aspirators, mentioned above, axial suction slots 12 being provided in these annular bulges which in the suction end of the aspirator form a portion of the tube wall, which is gently curved inwards and defines an end aperture the diameter of which is smaller than the inner diameter of the tube. The dental aspirator preferably has an outer diameter of about 6.5 mm in the smooth portions thereof, and the wall thickness of these portions preferably is of the order of 0.5–1 mm.

Figure 2:
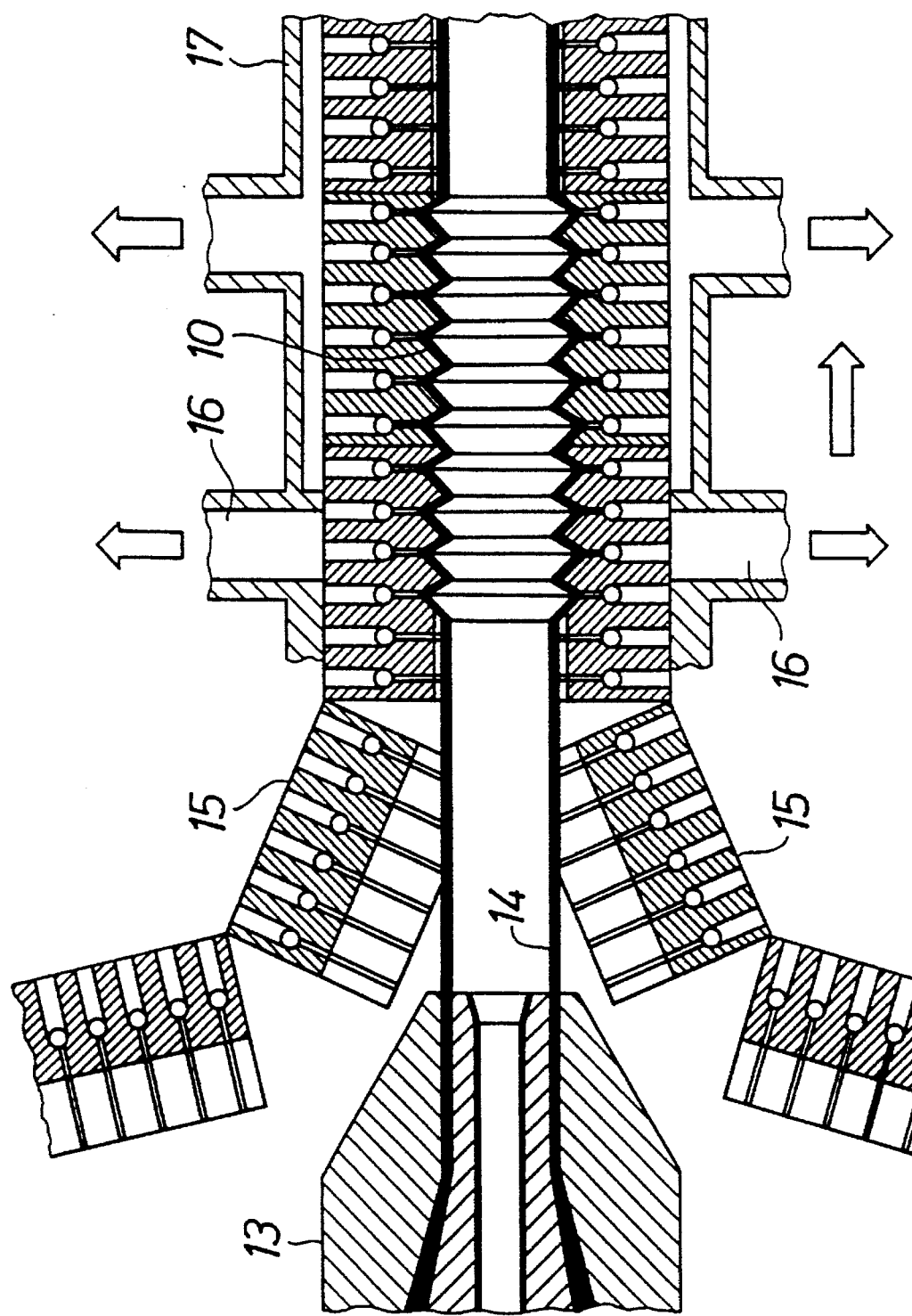
FIG. 2 is a horizontal cross sectional view of an extruder during the manufacture of the aspirator.

In FIG. 2 it is shown how the dental aspirator thus constructed is manufactured. From a conventional tube extruder the nozzle portion of which is partly shown at 13, a smooth tube 14 is extruded, which has the same dimension as the smooth portions of the dental aspirator. Immediately after the extrusion while the tube wall is still warm and soft the tube is enclosed at opposite sides by chilled mold chains 15 which are driven in an endless path and seal against each other around the tube 14. The machine can be of a known construction, made by Hegler, and the principle of an extruder having such chilled mold chains is well known and is disclosed inter alia in U.S. Pat. No. 3,538,209 referred to above. The chilled molds 15 are constructed in such a way that with a pitch corresponding to the length of the dental aspirator said molds shape the tube wall still soft in order to obtain the bellows portion 10 and the profiled portion 11, the rest of the tube wall being left with a smooth surface. The portions 10 and 11 can be shaped by a negative pressure being created in the cavities of the molds via suction passages 16 so that the soft tube wall is brought to follow the shape of the mold cavities, but it is also possible to press the tube wall against the mold cavities by inside pressure in the tube. However, in that case it is necessary that the tube during the extrusion slides over a sealing mandrel which is located at a distance downstream of the extruder and is anchored therein as is disclosed in said U.S. Pat. No. 3,538,209. While the shaped portions are enclosed by the molds these pass through a cooling envelope 17 for cooling the tube wall so that the wall will maintain the shape imparted to it.

Figure 3:
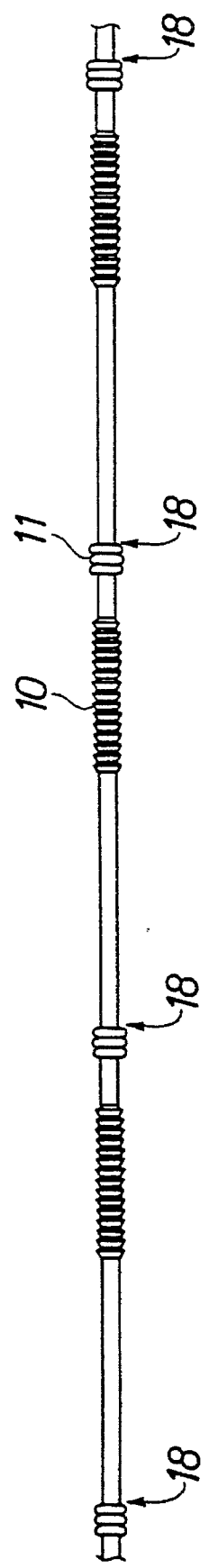
FIG. 3 is a side view of the continuous tube length leaving the extruder.
Figure 11:
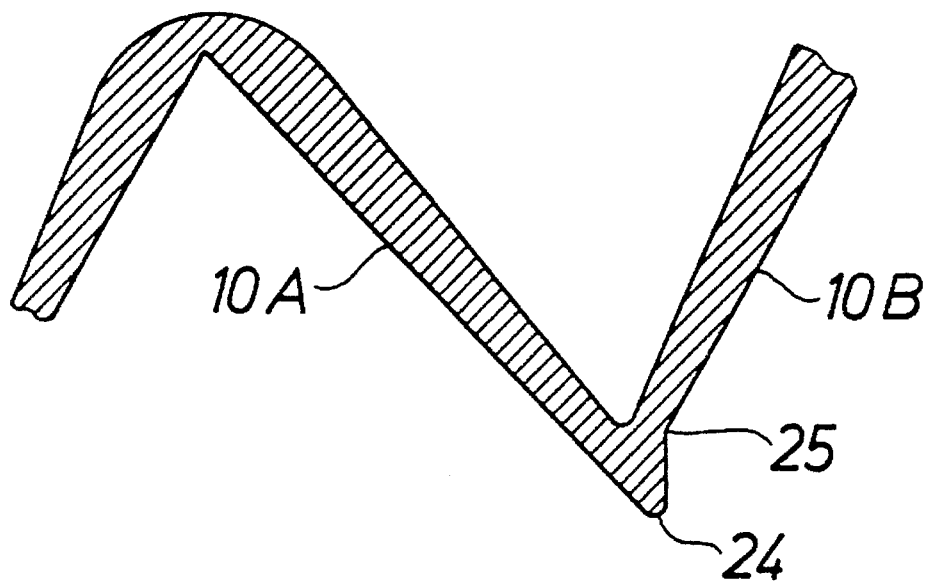
FIG. 11 is an enlarged axial cross sectional view of the wall of the bellows portion.

By applying this known technique which for the rest does not require a detailed description there is obtained a tube length according to FIG. 3, i.e. a length of integral dental aspirators according to FIG. 11. In connection with the extrusion this length can be worked in order to open slots 12, and when this has been done the tube length is cut at arrows 18 in order to obtain individual aspirators. The method thus makes possible that the dental aspirators are manufactured in a continuous length and that all work operations are performed in one and the same line without the necessity of transferring the tube length or the individual aspirators from one working station to the other. All working takes place while the tube length is passing from the extruder.

In the tube length according to FIG. 3 all dental aspirators are placed in one and the same direction, but it may be advantageous to have the aspirators placed alternatingly in one direction and the other so that the suction ends of two adjacent dental aspirators will be adjacent each other alternatingly with the ends to be connected to the suction hose being located adjacent each other. By this measure the packaging of the dental aspirators will be facilitated because it is desired to place the aspirators in the package alternatingly in one direction and the other in order to obtain a smooth package; if all aspirators are placed in the same direction the package will be thicker in the region of the bellows portion 10 and the profiled portion 11.

The shape of the profiled portion 11 can be varied in different manners. For example it is possible to provide suction apertures between the annular bulges which in that case are mutually spaced, instead of providing the slots 12. Also an embodiment according to FIGS. 4 and 5 is conceivable wherein axial flanges 19 are provided and have suction apertures 20. Also such flanges can be formed by means of the chilled molds 15, while the apertures 20 can be made after the profiled portion having left the chilled molds, either by drilling or by thermal perforation. Slots can be provided also in the flanges 19 instead of apertures. It is even possible within the scope of the invention to exclude the profiled portion at the suction end of the dental aspirator and replace such portion by a separately manufactured cage-shaped cover mounted afterwards to the aspirator, although this will make the aspirator essentially more expensive. Finally it should be mentioned that the profiled portion can be made as a bellows portion similar to the bellows portion 10, wherein suction apertures are provided in the annular grooves between the annular portions having the shape of truncated cones; also the suction end of the dental aspirator then can be adjusted to the work to be performed in the oral cavity by suitably bending the aspirator.

Figure 6:
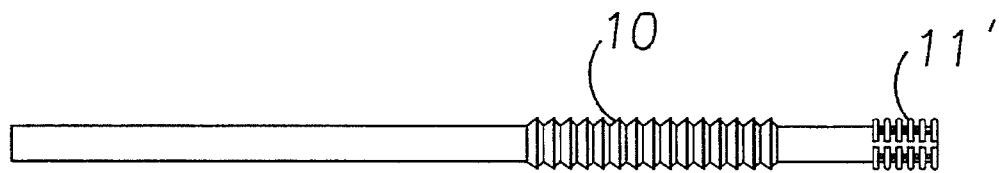
FIG. 6 is a sideview of a third embodiment of the dental aspirator to be manufactured by the method of the invention.
Figure 7:
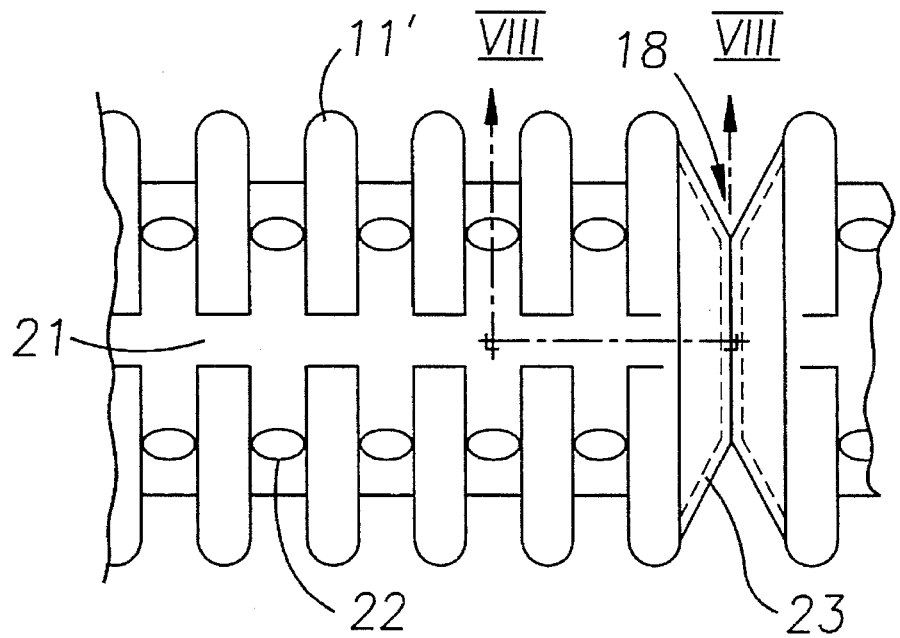
FIG. 7 is an enlarged fragmentary side view of two dental aspirators according to FIG. 6 integral at the suction ends.
Figure 8:
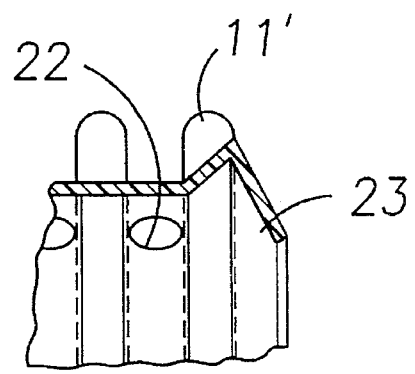
FIG. 8 is an enlarged portion within the lines enclosed by VIII—VIII in FIG. 7.
Figure 9:
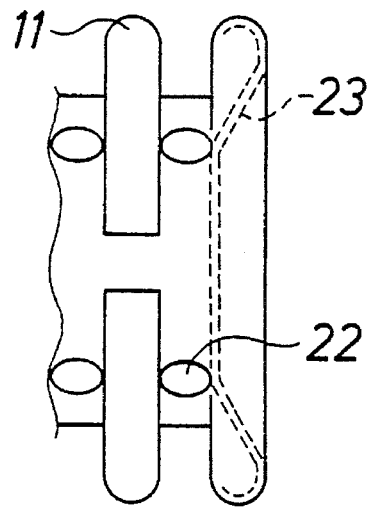

The dental aspirator according to FIG. 6 has in the suction end thereof a number of annular bulges 11' which are gently curved but do not extend over the total circumference of the aspirator; they extend over slightly less than half the circumference so that there are axial gaps 21 in the annual bulges. Between the bulges suction apertures 22 are provided. Preferably, the dental aspirator is manufactured in the manner described above with the aspirators placed alternatively in one direction and the other in the tube length so that the suction ends of two adjacent aspirators are located adjacent each other alternatingly with the ends to be connected to the suction hose being located adjacent each other. In FIG. 7 the suction ends of two dental aspirators are shown to be interconnected at end portions 23 shaped as truncated cones. The aspirators are separated by cutting at the arrow 18 the end portion having the shape of a truncated cone then being snapped into the aspirator as shown in FIG. 9 in order that the sharp edge where the aspirator has been cut will be located inside the aspirator and cannot cause irritation on the soft portions in the oral cavity.

Figure 10:
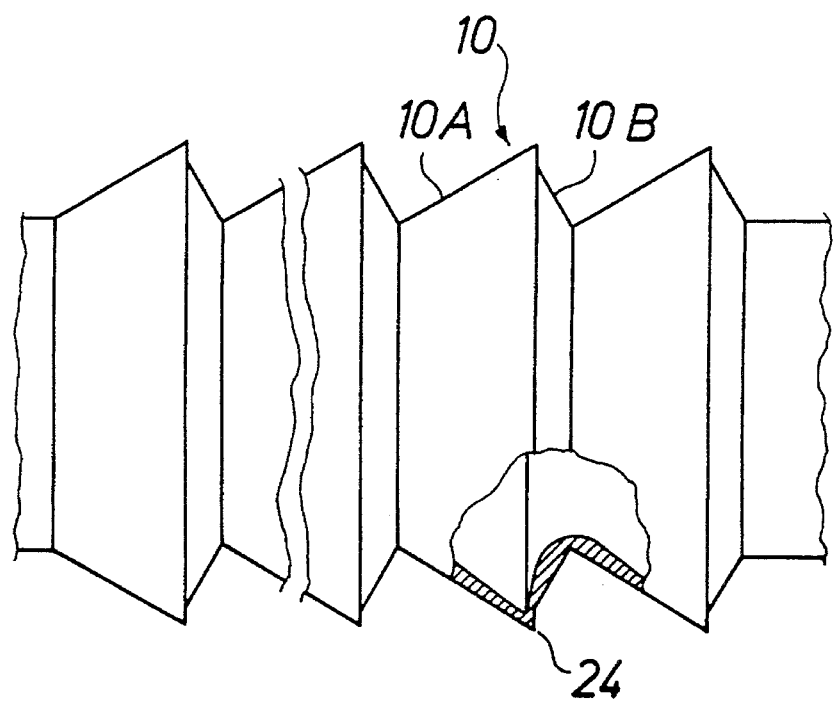
FIG. 10 is a side view, partly an axial cross sectional view, of the bellows portion of the dental aspirator according to FIG. 6.

In the dental aspirator of FIG. 6 the bellows portion 10 is made in a specific manner in order to facilitate bending of this portion. According to FIGS. 10 and 11 one of the two annular portions having a shape of a truncated cone and forming a fold in the bellows portion, said annular portions being indicated at 10A and 10B in FIGS. 10 and 11, is extended to form a collar 24 by the shaping in the shield molds. By this extension of the material there is obtained a thinning 25 in the transition between portions 10A and 10B, and this thinning forms a hinge considerably facilitating bending of the bellows portion.

Figure 12:
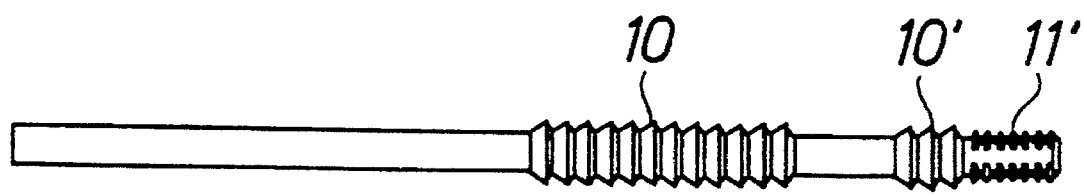
FIG. 12 is a side view of a fourth embodiment of the dental aspirator to be manufactured by the method of the invention.

The dental aspirator in FIG. 12 has a bellows portion 10 and an end portion in the suction end with annular bulges 11' in the same manner as the dental aspirator in FIG. 6 and additionally has a further bellows portion 10' adjacent the end portion formed with annular bulges at the suction end, said further bellows portion being axially spaced from portion 10. Due to the further bellows portion 10' the end portion at the suction end can be angled to a suitable position for the actual use of the aspirator.

Figure 13:
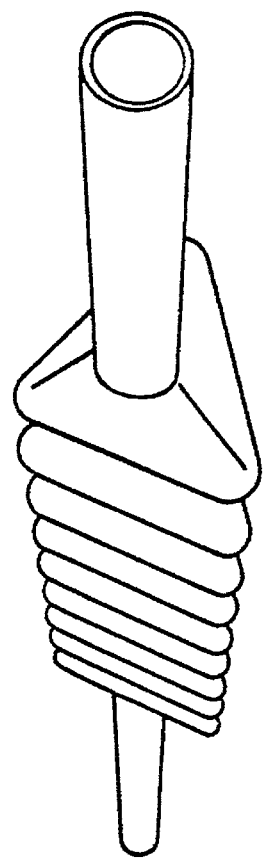
FIG. 13 is a perspective view of a fifth embodiment of the dental aspirator of the invention.
Figure 14:
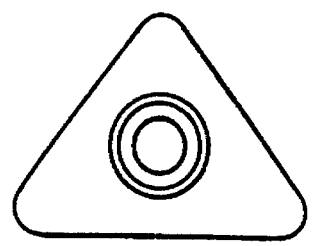
FIG. 14 is an end view of the aspirator in FIG. 13.

The bellows portion according to FIGS. 13 and 14 can have folds which are formed by two cupshaped portions having the shape of a truncated pyramid, the pyramid in this case having a triangular base. As in the embodiments described above the two portions having the shape of a truncated pyramid and forming a fold shall have the concave surfaces facing each other and one portion shall have a smaller width than the other portion so as to be snapped completely or partly into said latter portion. Bending of the aspirator in the bellows portion in this case will be determined by the three sides of the pyramid base, which means that the dental aspirator can be bent only in one of the three directions determined by these sides. However, the pyramid base can have more than three sides.

I claim:

1. Method for manufacturing a plurality of plastic dental aspirators comprising the steps of
    (a) extruding a smooth plastic continuous length tube,
    (b) shaping the continuous length tube into a plurality of the dental aspirators by enclosing the continuous length tube within chilled mold chains while the continuous length tube is still warm and soft, driving the chilled mold chains in an endless path and sealing each other around the continuous length tube to form a bellows portion and a profiled portion for each dental aspirator, the bellows portion spaced from the ends of the dental aspirator and limited to a minor portion of the dental aspirator length, a major portion of the dental aspirator length having a smooth surface, the bellows portion containing multiple folds, each fold having a first and a second cup-shaped portion with opposed concave surfaces, the first cup-shaped portion having a smaller width than the second cup-shaped portion in order to be snapped into the second cup-shaped portion when the dental aspirator is bent in the bellows portion for maintaining a bow,
    (c) cutting the continuous length tube at a separation point between each axially adjacent dental aspirator adjacent the profiled portion to form a plurality of separate dental aspirators, the separation point forming an end portion of a suction end of each separate dental aspirator.

2. Method according to claim 1 wherein the cup-shaped portions are shaped as truncated cones or pyramids.

3. Method according to claim 1 wherein axial bulges are made in the continuous length tube during the shaping step in the profiled portion, and perforating the bulges as the continuous length tube is moved axially and before the cutting step.

4. Method according to claim 1 wherein annular bulges are formed in the profiled portion by the mold chains and a perforation in a wall of the continuous length tube is made in or between the annular bulges as the continuous length tube is moved axially and before the cutting step.

5. Method according to claim 2 wherein axial bulges are formed in the profiled portion by the mold chains, and perforating the bulges as the continuous length tube is moved axially and before the cutting step.

6. Method according to claim 2 wherein annular bulges are formed in the profiled portion by the mold chains and a perforation of the tube wall is made in or between the annular bulges as the continuous length tube is moved axially and before the cutting step.

7. Method according to claim 1 wherein during the shaping of the continuous length tube a portion of a wall of the continuous length tube is gently curved inward as a termination of the profiled portion adjacent the separation point where the continuous length tube is cut to separate dental aspirators.

8. Method according to claim 2 wherein during the shaping of the continuous length tube a portion of a wall of the continuous length tube is gently curved inward as a termination of the profiled portion adjacent the separation point where the continuous length tube is cut to form separate dental aspirators.

9. Method according to claim 3 wherein during the profiling of a wall of the continuous length tube a portion of the wall of the continuous length tube is gently curved inward as a termination of the profiled portion adjacent the separation point where the continuous length tube is cut to form separate dental aspirators.

10. Method according to claim 4 wherein during the shaping of the profiled portion a portion of a wall of the continuous length tube is gently curved inward as a termination of the profiled portion adjacent the separation point where the continuous length tube is cut to form separate dental aspirators.

11. Method according to claim 1 wherein during the shaping of a wall of the continuous length tube a portion of the wall is shaped as a truncated cone as a termination of the profiled portion adjacent to the separation point where the continuous length tube is cut to form separate dental aspirators.

12. Method according to claim 2 wherein during the shaping of a wall of the continuous length tube a portion of the wall is shaped as a truncated cone as a termination of the profiled portion adjacent to the separation point where the continuous length tube is cut to form separate dental aspirators.

13. Method according to claim 3 wherein during the shaping of a wall of the continuous length tube a portion of the wall is shaped as a truncated cone as a termination of the profiled portion adjacent to the separation point where the continuous length tube is cut to form separate dental aspirators.

14. Method according to claim 4 wherein during the shaping of a wall of the continuous length tube a portion of the wall is shaped as a truncated cone as a termination of the profiled portion adjacent to the separation point where the continuous length tube is cut to form separate dental aspirators.

15. Method according to claim 1 wherein one of the two cup-shaped portions which form a fold of the bellows portion is extended to form a collar, and a thinned portion functioning as a hinge is formed in a transition zone between the two cup-shaped portions.

* * * * *